(12) United States Patent
Westdyk

(10) Patent No.: US 9,820,832 B2
(45) Date of Patent: Nov. 21, 2017

(54) VERTICALLY ADJUSTABLE ROTATIONAL STABILIZER FOR A DISPOSABLE ARTICULATOR

(71) Applicant: Advanced Articulators (Pty) Ltd, Highveld (ZA)

(72) Inventor: Alan Michael Westdyk, Faerie Glen (ZA)

(73) Assignee: Advanced Articulators (Pty) Ltd, Highveld (ZA)

( * ) Notice: Subject to any disclaimer, the term of this patent is extended or adjusted under 35 U.S.C. 154(b) by 406 days.

(21) Appl. No.: 14/379,042

(22) PCT Filed: Feb. 18, 2013

(86) PCT No.: PCT/IB2013/051304
§ 371 (c)(1),
(2) Date: Aug. 15, 2014

(87) PCT Pub. No.: WO2013/121402
PCT Pub. Date: Aug. 22, 2013

(65) Prior Publication Data
US 2015/0024338 A1 Jan. 22, 2015

(30) Foreign Application Priority Data
Feb. 17, 2012 (ZA) ................. 2012/01203

(51) Int. Cl.
*A61C 11/02* (2006.01)
*A61C 11/00* (2006.01)

(52) U.S. Cl.
CPC ............ *A61C 11/003* (2013.01); *A61C 11/02* (2013.01)

(58) Field of Classification Search
CPC ..... A61C 11/003; A61C 11/02; A61C 11/022; A61C 11/025
See application file for complete search history.

(56) References Cited

U.S. PATENT DOCUMENTS 2,234,411 A * 3/1941 McDonald ............. A61C 11/02
433/60
2,423,522 A * 7/1947 Shmukler ............. A61C 11/02
433/58

(Continued)

FOREIGN PATENT DOCUMENTS

DE 2511388 B1 5/1976
DE 19530157 A1 4/1996
JP 2008113717 A 5/2008

OTHER PUBLICATIONS

International Search Report for PCT/IB2013/051304 dated Jun. 10, 2014, 4 pages.

*Primary Examiner* — Ralph Lewis
(74) *Attorney, Agent, or Firm* — Fitch, Even, Tabin & Flannery LLP

(57) ABSTRACT

A vertically adjustable rotational stabilizer (10) for a disposable articulator is provided. The articulator comprises a hinged pair of support arms, each support arm having a proximal end and a distal end, with the proximal ends of the support arms being hingedly fitted together. Each arm defines an opening or cavity between its distal and proximal ends. The vertically adjustable rotational stabilizer (10), in broad terms, comprises at least one body (30, 66) secured or securable to the support arms (14, 16) and positioned substantially within the opening defined by the support arm, and an elongate member (56) being adjustable relative to the at least one body so as to adjust and fix the distance between the distal ends of the support arms (14, 16).

14 Claims, 20 Drawing Sheets

(56) References Cited

U.S. PATENT DOCUMENTS

| | | | |
|---|---|---|---|
| 2,510,152 A * | 6/1950 | Stoll | .................. A61C 11/02 33/513 |
| 4,058,895 A | 11/1977 | Mack et al. | |
| 4,214,367 A | 7/1980 | Mack et al. | |
| 4,687,442 A | 8/1987 | Wong | |

* cited by examiner

VERTICALLY ADJUSTABLE ROTATIONAL STABILIZER FOR A DISPOSABLE ARTICULATOR

CROSS REFERENCE TO RELATED APPLICATIONS

This application is a national phase application of International Application No. PCT/IB2013/051304, filed Feb. 18, 2013, designating the United States and claiming priority to South African Patent Application No. 2012/01203, filed Feb. 17, 2012, both of which are incorporated by reference as if fully rewritten herein.

FIELD OF THE INVENTION

This invention relates to a vertically adjustable rotational stabilizer for a disposable articulator.

BACKGROUND TO THE INVENTION

A disposable articulator is a mechanical device used in dentistry to which casts of the maxillary (upper) and mandibular (lower) teeth are fixed, reproducing recorded positions of the mandible in relation to the maxilla. A disposable articulator assists in the fabrication of removable prosthodontic appliances (dentures), fixed prosthodontic restorations (crowns, bridges, inlays and onlays) and orthodontic appliances.

In one version of the disposable articulator, after an impression has been poured up, it is directly mounted on a plastic base or tray that already has a built-in condyle to form a complete articulator when the two halves are joined. However, at present, this type of articulator does not have a vertical rotational adjustment arrangement to adjust the separation of the two halves of the articulator. The present invention aims to address this shortcoming.

SUMMARY OF THE INVENTION

According to the invention there is provided a vertically adjustable rotational stabilizer for a disposable articulator, the articulator comprising a hinged pair of support arms, each support arm having a proximal end and a distal end, with the proximal ends of the support arms being hingedly fitted together, each arm defining an opening or cavity between its distal and proximal ends, the vertically adjustable rotational stabilizer, in broad terms, comprising at least one body secured or securable to the support arms and positioned substantially within the opening defined by the support arm, and an elongate rotational member being adjustable relative to the at least one body so as to adjust and fix the distance between the distal ends of the support arms.

In an embodiment, the stabilizer comprises:
- a first body secured or securable to one of the support arms and positioned substantially within the opening defined by the support arm, the first body defining a seat with an aperture therein;
- a first swivel body that can swivel within the seat of the first body, the first swivel body having a bore that can align with the aperture in the seat of the first body;
- an elongate rotational adjusting member having a proximal end and a distal end and being arranged to snugly extend through, and be adjustable relative to, the bore of the first swivel body, the elongate rotational adjusting member also being arranged to extend through the aperture in the seat of the first body when the elongate rotational adjusting member and the first swivel body are seated within the seat of the first body; and
- a second body secured or securable to the other support arm and positioned substantially within the opening defined by the support arm, the second body defining a receiving surface against which the distal end of the elongate rotational adjusting member can abut, thereby allowing the relative distance between the distal ends of the support arms to be adjusted.

In an embodiment, the first swivel body is a truncated sphere that defines two substantially flat faces, with the bore extending through the flat faces of the first swivel body. The first swivel body further comprises a pair of lugs extending from opposite sides of the first swivel body.

In an embodiment, the seat of the first body includes a pair of curved side walls with an elongate groove therebetween so as to define the aperture, the curved side walls defining an aperture and/or a slot to receive the lugs of the first swivel body, the curved side walls thus accommodating the first swivel body to enable the first swivel body to swivel within the seat of the first body around an axis defined by the lugs.

In an embodiment, the first body includes a pawl proximate the aperture of the seat, and the first swivel body comprises a plurality of teeth on an exterior surface (approximately midway between the lugs and in line with the bore) so as to define a ratchet to facilitate the correct orientation of the first swivel body relative to the first body.

In an embodiment, the elongate rotational adjusting member comprises a handle portion proximal its proximal end and a threaded shank extending from the handle portion and terminating in its distal end, with the bore of the first swivel body being complementarily threaded with respect to the threaded shank, so that the adjusting member is adjustable relative to the first swivel body.

In an embodiment, the second body comprises a socket having a curved receiving surface. In an embodiment, the curved receiving surface comprises ridges/slots against which the distal end of the elongate rotational adjusting member can rest/grip.

In an alternate embodiment, the second body defines a seat with an aperture therein, with a second swivel body being able to swivel within the seat of the second body, the second swivel body comprising a socket having a curved receiving surface against which the distal end of the elongate rotational adjusting member can rest/grip.

In one version, the first and second bodies take the form of clip bodies that can be secured or removably clipped onto (or rest on or be supported by or glued to) the support arms. In this version, the first and second bodies comprise clipping formations to enable them to be clipped onto the support arms. The clipping formations comprise deformable lugs on either side of the bodies, which can be snap fitted into corresponding recesses defined in the support arms.

In an alternate version, the first and second bodies are integrally formed with the support arms.

BRIEF DESCRIPTION OF THE DRAWINGS

The invention will be described, by way of example only, with reference to the accompanying drawings in which.

DETAILED DESCRIPTION OF THE DRAWINGS

Figure 1:
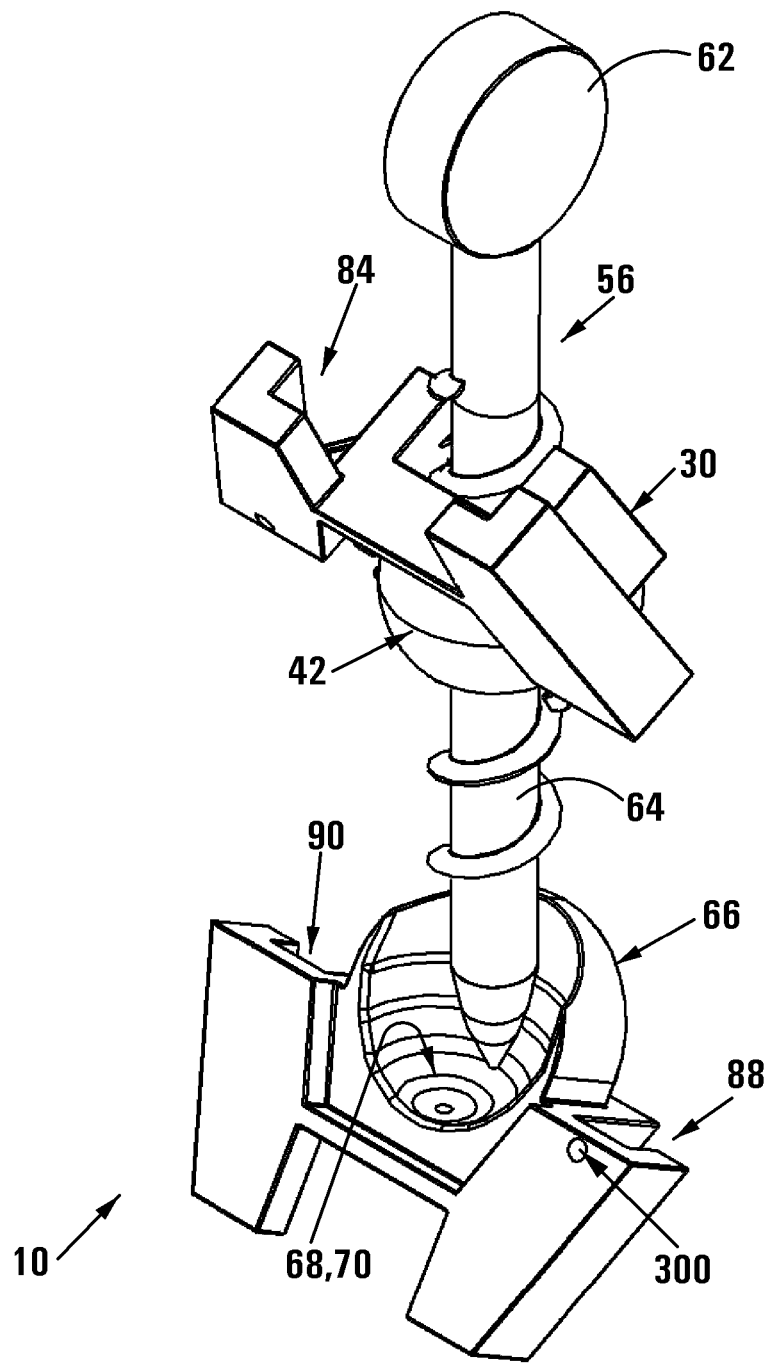
FIG. 1 shows a perspective view of a vertically adjustable rotational stabilizer for a disposable articulator, according to a first embodiment of the present invention.

Referring first to FIG. 1 there is provided a vertically adjustable rotational stabilizer 10 for a disposable articulator, according to a first embodiment of the present invention. An example articulator 12 to which the stabilizer 10 shown in FIG. 1 can be fitted will now be described with reference to FIG. 8. The articulator 12 comprises a hinged pair of support arms 14, 16, each support arm 14, 16 having a proximal end 18 and a distal end 20, with the proximal ends 18 of the support arms 14, 16 being hingedly fitted together with a thin walled hinge 22. Each arm 14, 16 defines an opening or cavity 24, 26 between its proximal and distal ends 18, 20.

Figure 2:
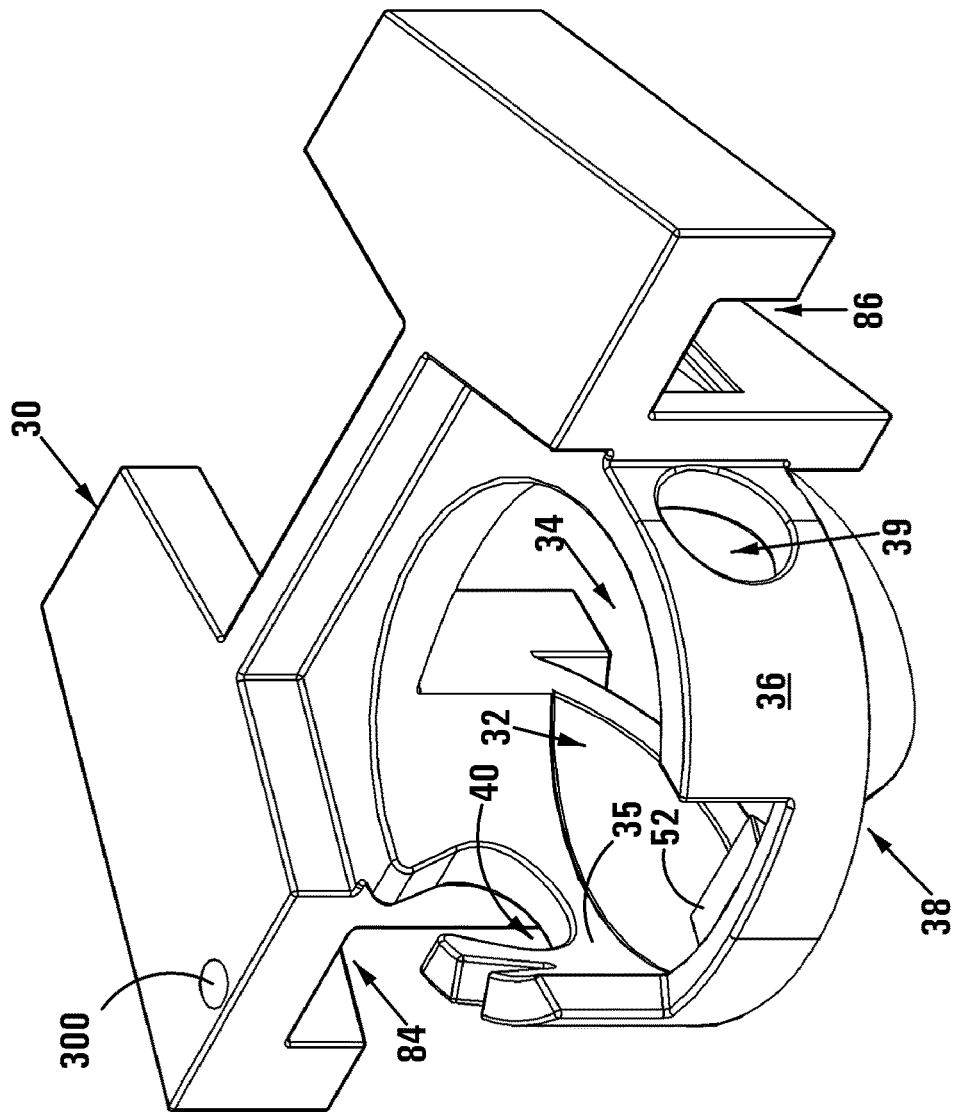
FIG. 2 shows a perspective view of a first, upper body of the stabilizer shown in FIG. 1.
Figure 8:
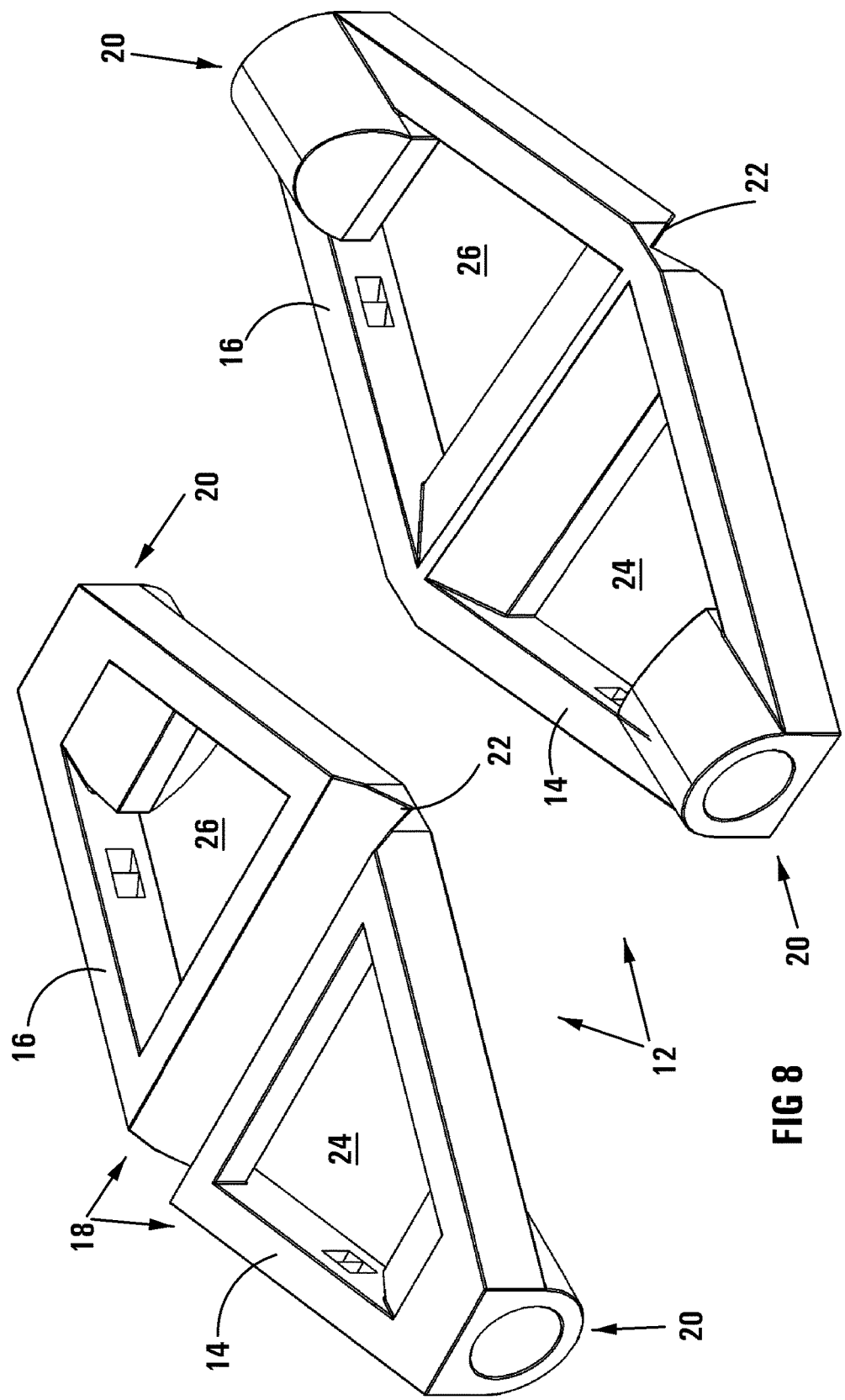
FIG. 8 shows a perspective view of an example articulator to which the stabilizer shown in FIG. 1 can be fitted.

Referring back to FIG. 1 and also to FIG. 2, the vertically adjustable rotational stabilizer 10 comprises a first, upper body 30 secured or securable to one of the support arms 14 of the articulator 12 in FIG. 8. The first body 30 is arranged to be positioned substantially within the opening 24 defined by the support arm 14, the first body 30 defining a seat 32 with an elongate, rectangular aperture 34.

Figure 3:
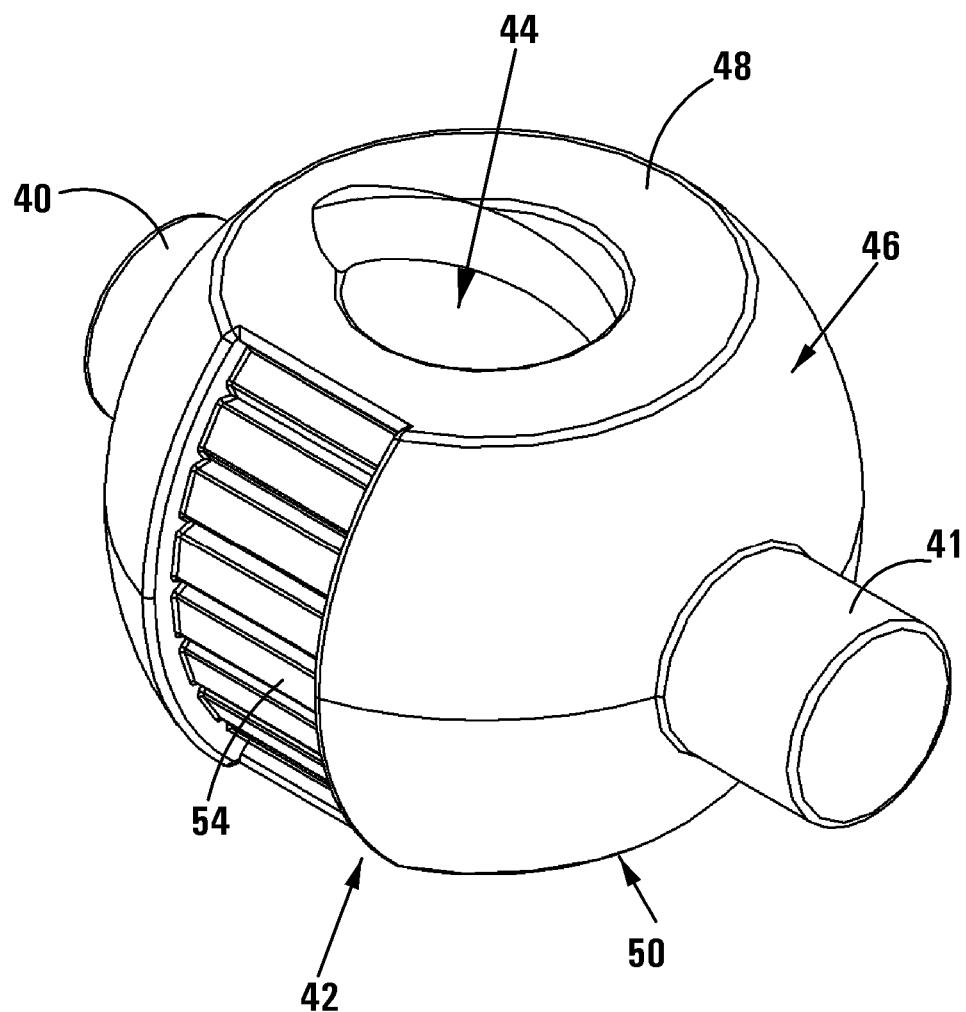
FIG. 3 shows a perspective view of a swivel body of the stabilizer shown in FIG. 1.

In an embodiment, the seat 32 of the first body 30 includes a pair of curved side walls 35, 36 with an elongate groove 38 therebetween so as to define the aperture 34. With reference now also to FIG. 3, the curved side walls 35, 36 define an aperture 39 and a slot 40 to receive the lugs 40, 41 of a first swivel body 42, which shall be described in more detail further below. In an alternative embodiment, the curved side walls 35, 36 may define a pair of slots (similar to slot 40) to receive the lugs 40, 41 of a first swivel body 42.

The curved side walls 35, 36 thus accommodate the first swivel body 42 to enable the first swivel body 42 to swivel within the seat 32 of the first body 30 around an axis defined by the lugs 40, 41. The first swivel body 42 has a bore 44 that can align with the aperture 34 in the seat 32 of the first body 30.

In an embodiment, the first swivel body 42 is a truncated sphere 46 that defines two substantially flat faces 48, 50, with the bore 44 extending through the flat faces 48, 50 of the first swivel body 42. The lugs 38, 40 extend from opposite sides of the first swivel body 42.

In an embodiment, the first body 30 includes a pawl 52 proximate the aperture 34 of the seat 32. The first swivel body 42 comprises a plurality of teeth 54 on an exterior surface (approximately midway between the lugs 40, 41 and in line with the bore 44) so as to define a ratchet to facilitate the correct orientation of the first swivel body 42 relative to the first body 30. This ratchet arrangement allows the first upper body 30 to determine the resting position of the stabilizer 10.

In particular, the elongate aperture 34 guides the stabilizer 10 along a defined path to stabilize the distance between two points in a given direction of motion. This elongate aperture 34 also predetermines the vertical adjustment of the distal ends 20 of the support arms 14, 16 of the articulator 12 from a minimum to a maximum elevation. Clearly, the greater the angle between the support arms 14, 16, the greater the rotational arc of the guiding aperture 34, and vice versa. In particular, the smaller the angle between the support arms 14, 16, the smaller the rotational arc to a minimum vertical position. The rectangular aperture 34 thus allows the stabilizer 10 the freedom to rotate to achieve a maximum and a minimum position. The vertical adjustable rotational vertical stabilizer 10 thus allows lateral, protrusive and orbital movement.

Figure 4:
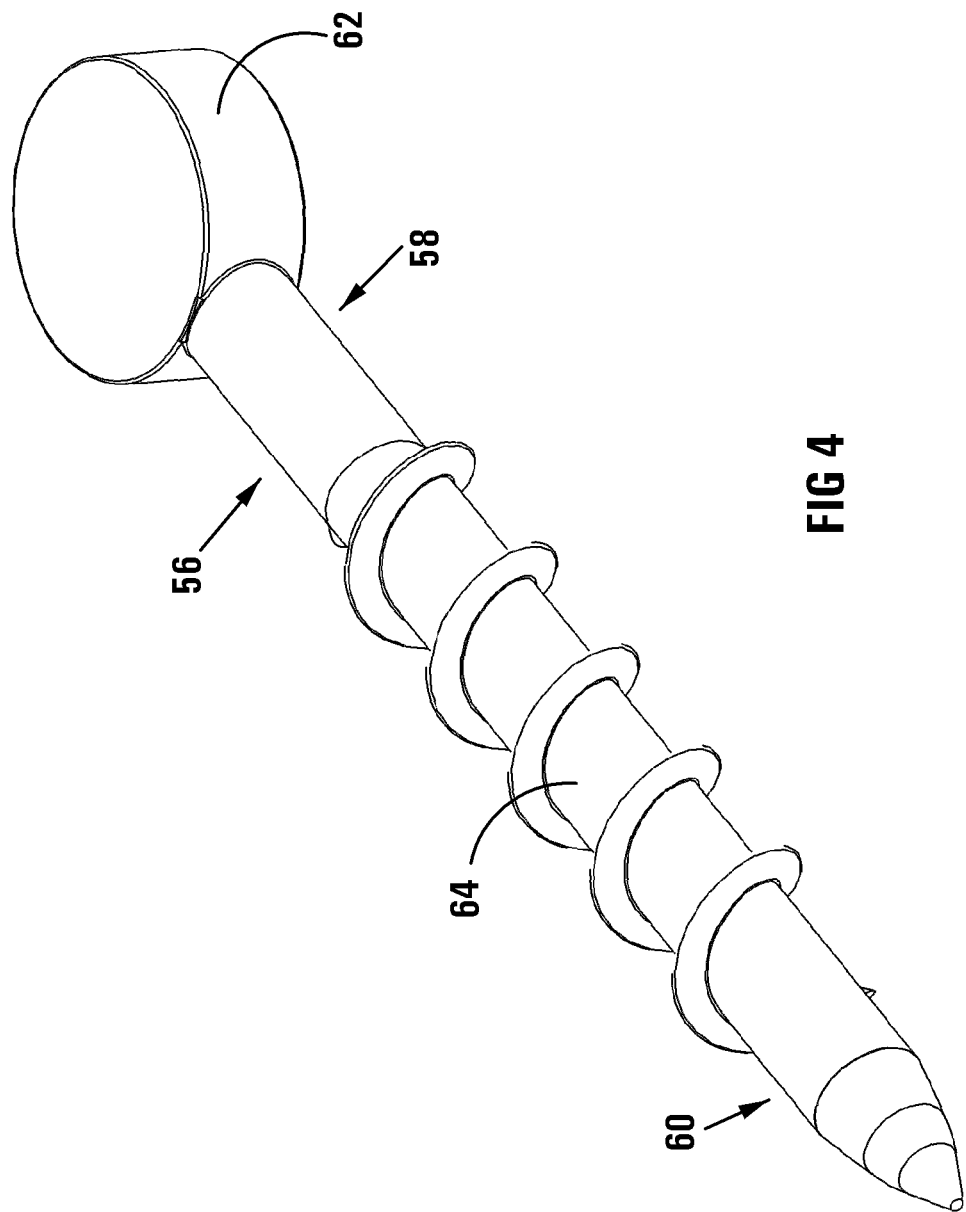
FIG. 4 shows a perspective view of an rotational adjusting member of the stabilizer shown in FIG. 1.

Referring now also to FIG. 4, the stabilizer 10 further comprises an elongate rotational adjusting member 56 having a proximal end 58 and a distal end 60. The member 56 is arranged to snugly extend through, and be adjustable relative to, the bore 44 of the first swivel body 42. The elongate rotational adjusting member 56 is also arranged to extend through the elongate, rectangular aperture 34 in the seat 32 of the first body 30 when the elongate rotational adjusting member 56 and the first swivel body 42 are seated within the seat 32 of the first body 30, as shown in FIG. 1.

In an embodiment, the elongate rotational adjusting member 56 comprises a handle portion 62 proximal its proximal end 58 and a threaded shank 64 extending from the handle portion 62 and terminating at its distal end 60. The bore 44 of the first swivel body 42 is complementarily threaded with respect to the threaded shank 64, so that the rotational adjusting member 56 is adjustable (and fixable) relative to the first swivel body 42.

Figure 5:
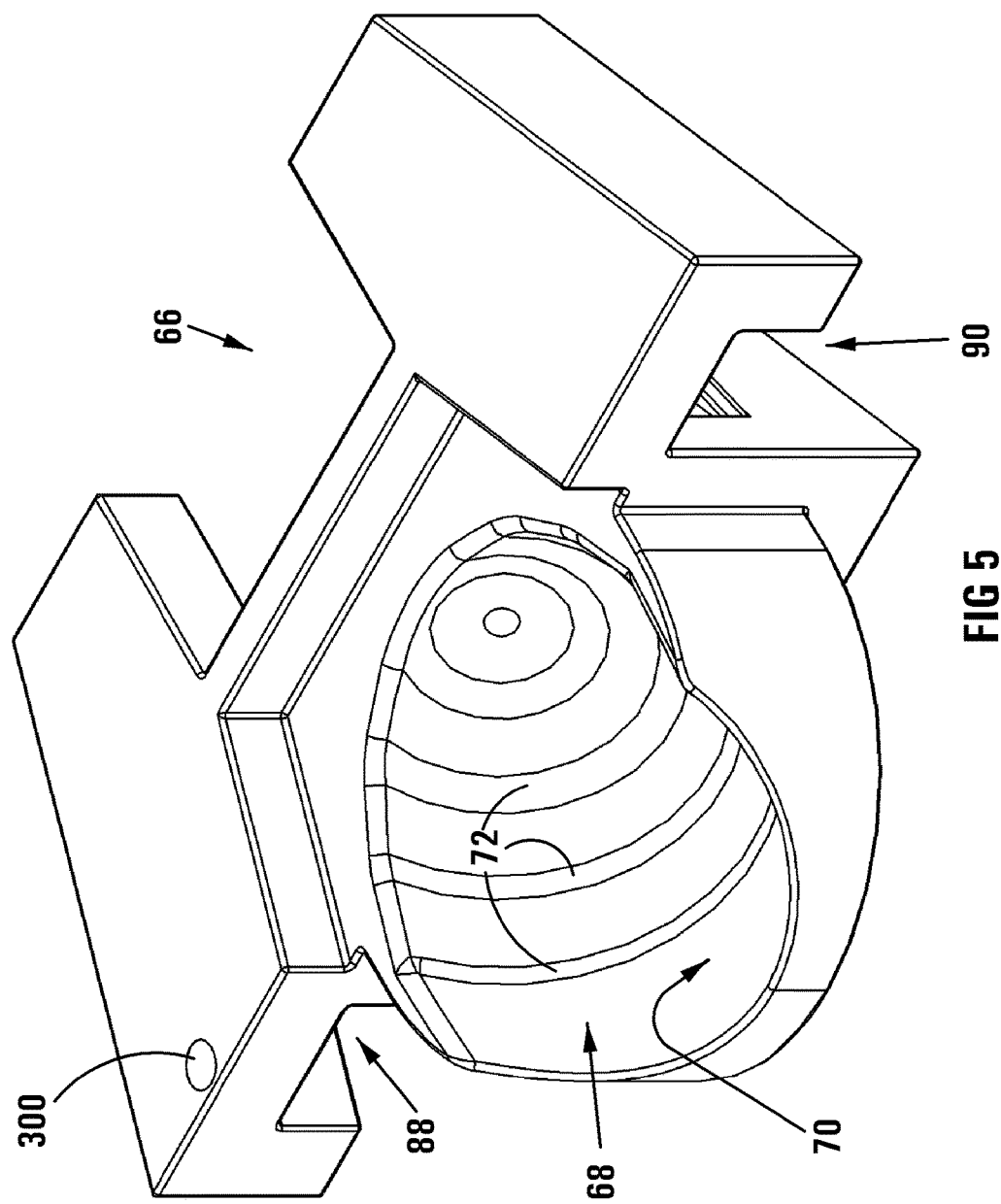
FIG. 5 shows a perspective view of a second, lower body of the stabilizer shown in FIG. 1.

Referring now also to FIG. 5, the stabilizer 10 further comprises a second, lower body 66 secured or securable to the other support arm 16 of the articulator 12 and positioned substantially within the opening 26 defined by the support arm 16. The second body 66 defines a receiving surface 68 against which the distal end 60 of the elongate rotational adjusting member 56 can abut, as shown in FIG. 1. The entire stabilizer 10 thus allows the relative distance between the distal ends 20 of the support arms 14, 16 of the articulator 12 to be adjusted (and fixed), as described above.

In an embodiment, the second body 66 comprises a socket 70 having a curved receiving surface 68. In an embodiment, the curved receiving surface 68 comprises formations 72 (typically, ridges and/or slots) against which the distal end 60 of the elongate rotational adjusting member 56 can rest/grip.

Figure 6:
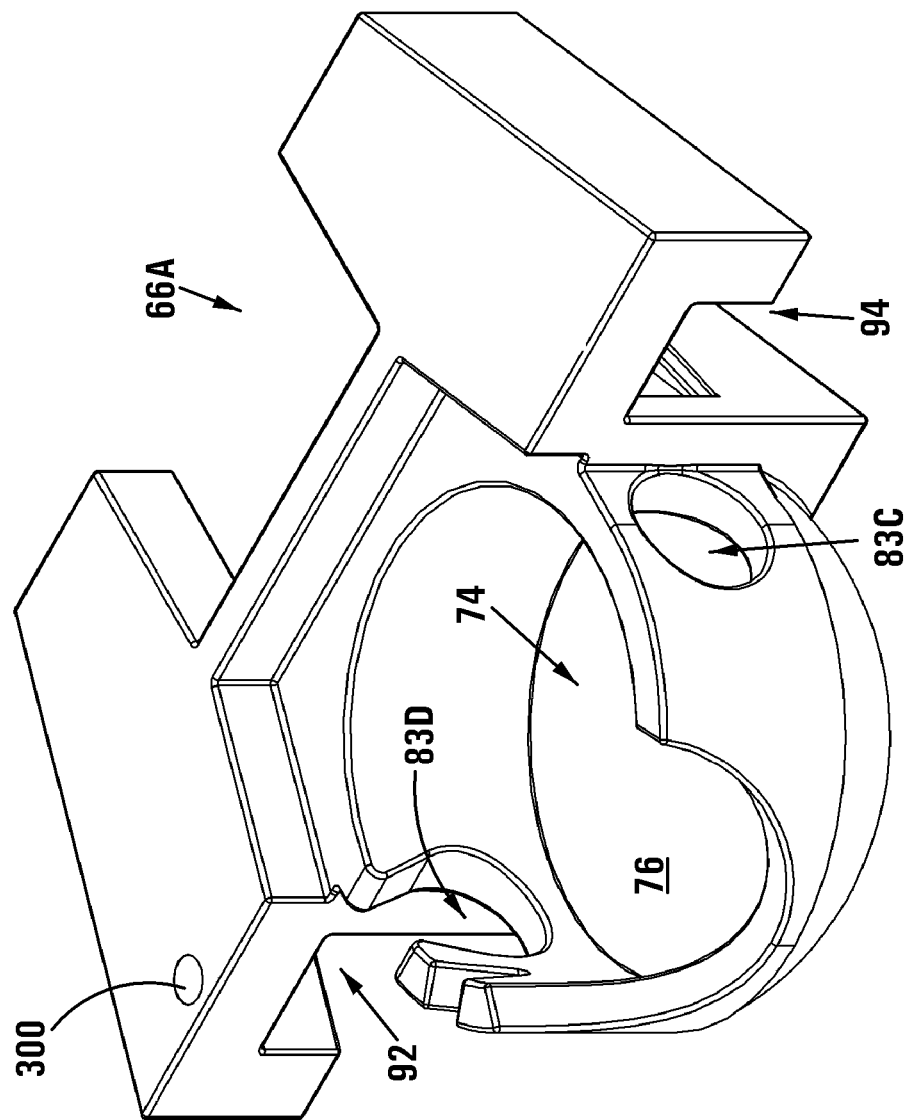
FIGS. 6 and 7 show perspective views of an alternative second, lower body that may be used with the stabilizer shown in FIG. 1.
Figure 7:
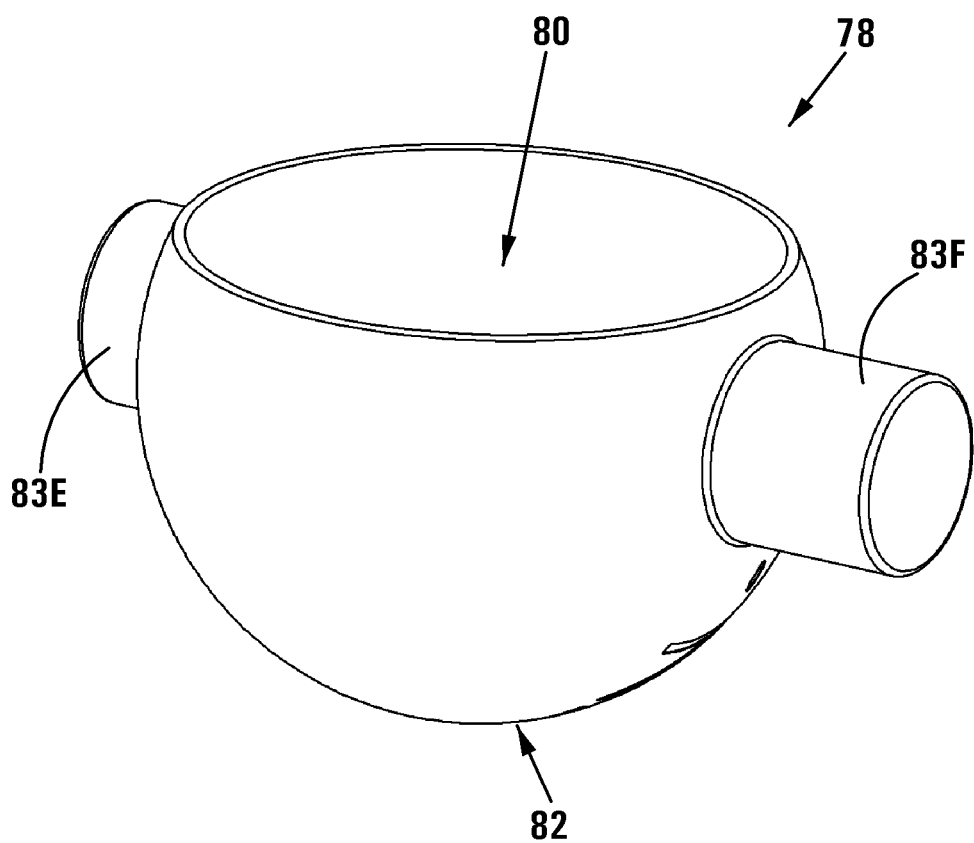

In an alternate embodiment, with reference now to FIGS. 6 and 7, a modified second body 66A defines a seat 74 with a round aperture 76 therein. A second swivel body 78 is thus able to swivel within the seat 74 of the second body 66, the second swivel body 78 comprising a socket 80 having a curved receiving surface 82 against which the distal end 60 of the elongate rotational adjusting member 56 can rest/grip. The seat 74 of the modified second body 66A includes a pair of curved side walls 83A, 83B, the curved side walls 83A, 83B defining an aperture 83C and a slot 83D to receive the lugs 83E, 83F of the second swivel body 78. Alternatively, the pair of curved side walls 83A, 83B may define a pair of slots, similar to slot 83D, to receive the lugs 83E, 83F of the second swivel body 78.

The curved side walls 83A, 83B thus accommodate the second swivel body 78 to enable the second swivel body 78 to swivel within the seat 74 of the second body 66A around an axis defined by the lugs 83E, 83F. This alternate embodiment is particularly useful for patients with extreme dental conditions.

In one version, the first and second bodies 30, 66, 66A take the form of clip bodies that can be secured to or removably clipped onto the support arms 14, 16 of the articulator 12. In this version, the first and second bodies 30, 66 comprise clipping formations 84 and 86, 88 and 90, and 92 and 94, respectively, to enable them to be clipped onto the support arms 14, 16. The clipping formations may comprise deformable lugs on either side of the bodies 30, 66, which can be fitted into corresponding recesses defined in the support arms 14, 16.

Alternatively, it is envisaged that the clip bodies can simply rest on or be supported by or be glued to the support arms 14, 16.

Although not shown, in an alternate version, the first and second bodies 30, 66 may be integrally formed with the support arms 14, 16 of the articulator 12.

Figure 9:
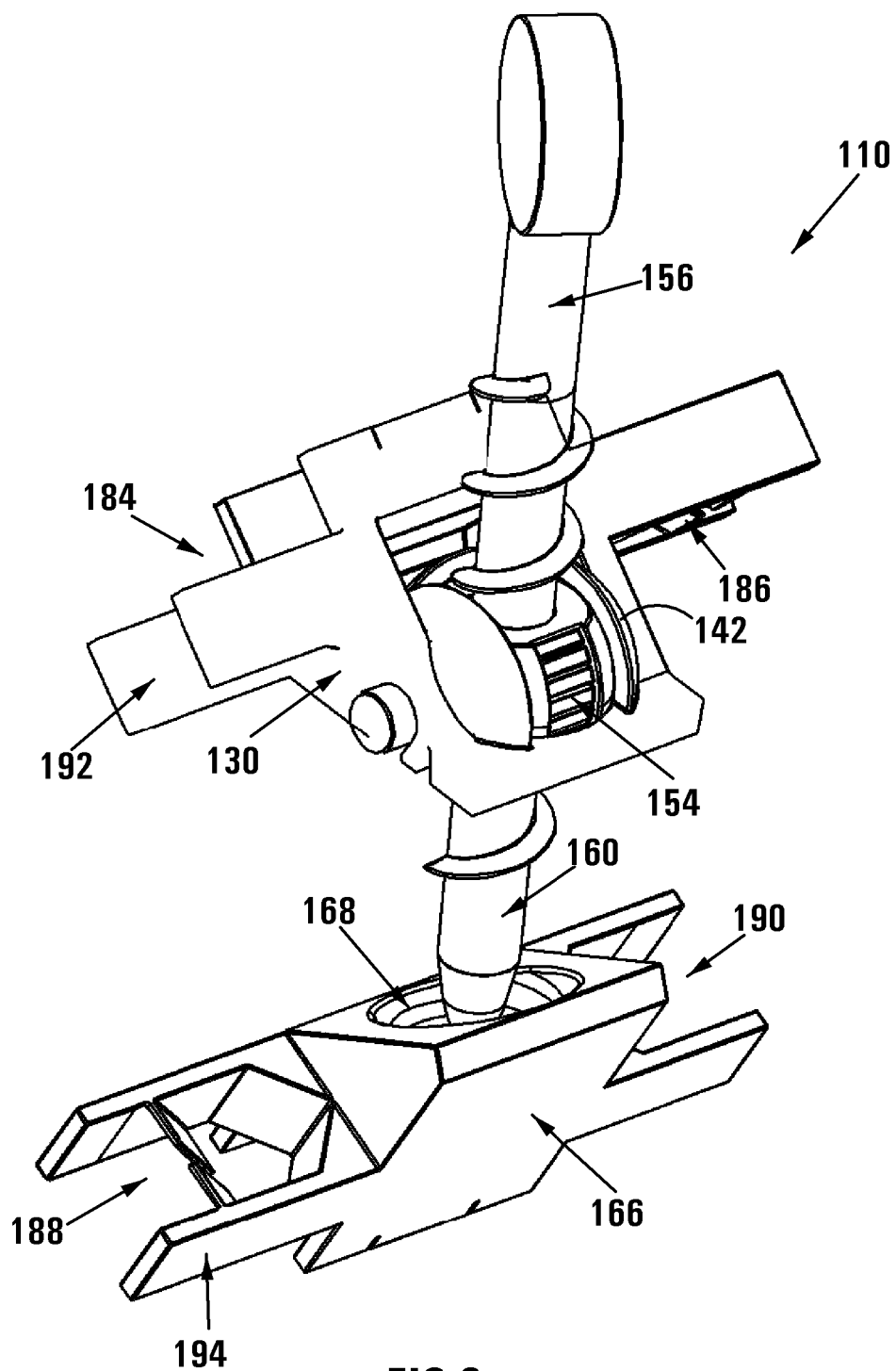
FIG. 9 shows a perspective view of a vertically adjustable rotational stabilizer for a disposable articulator, according to a second embodiment of the present invention.

Referring now to FIG. 9 there is provided a vertically adjustable rotational stabilizer 110 for a disposable articulator, according to a second embodiment of the present invention. An example articulator 112 to which the stabilizer 110 shown in FIG. 9 can be fitted will now be described with reference to FIG. 12. The articulator 112 comprises a hinged pivotal pair of support arms 114, 116, each support arm 114, 116 having a proximal end 118 and a distal end 120, with the proximal ends 118 of the support arms 114, 116 being pivotally fitted together with pivot pins 122. Each arm 114, 116 defines an opening or cavity 124, 126 between its proximal and distal ends 118, 120.

Figure 10:
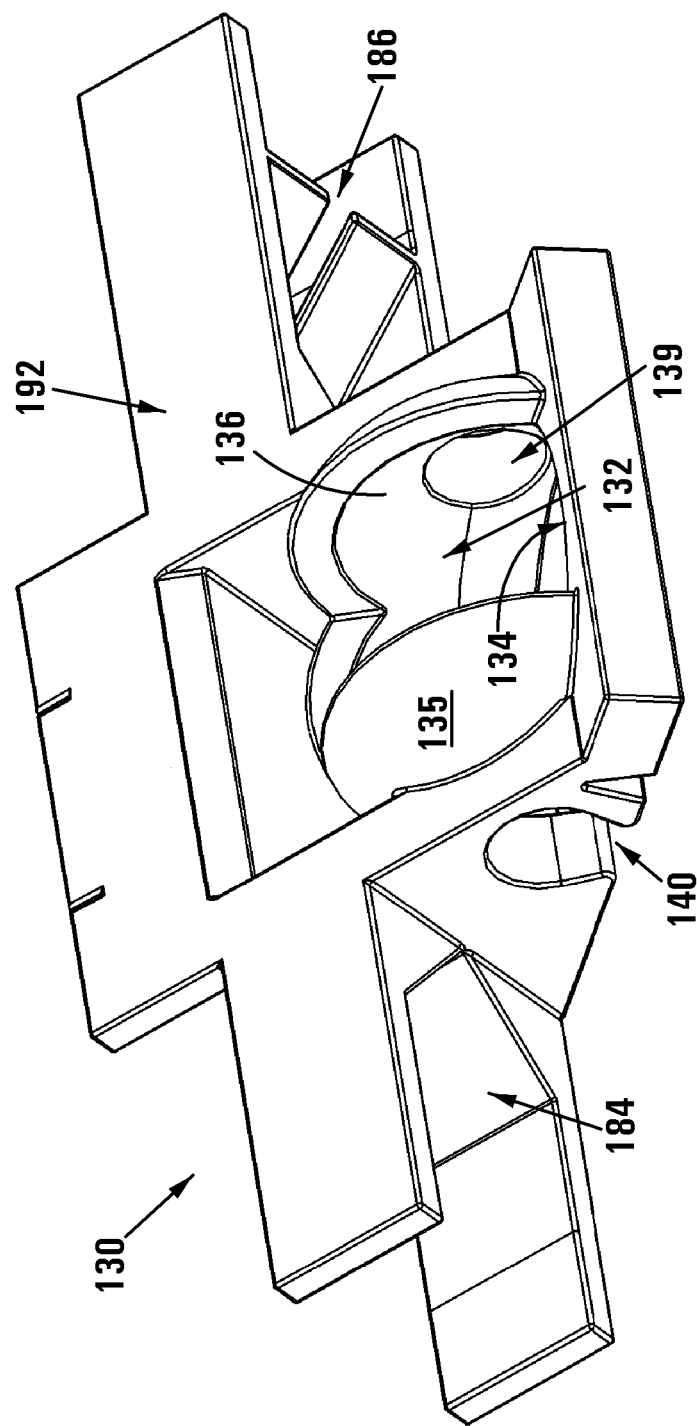
FIG. 10 shows a perspective view of a first, upper body of the stabilizer shown in FIG. 9.
Figure 12:
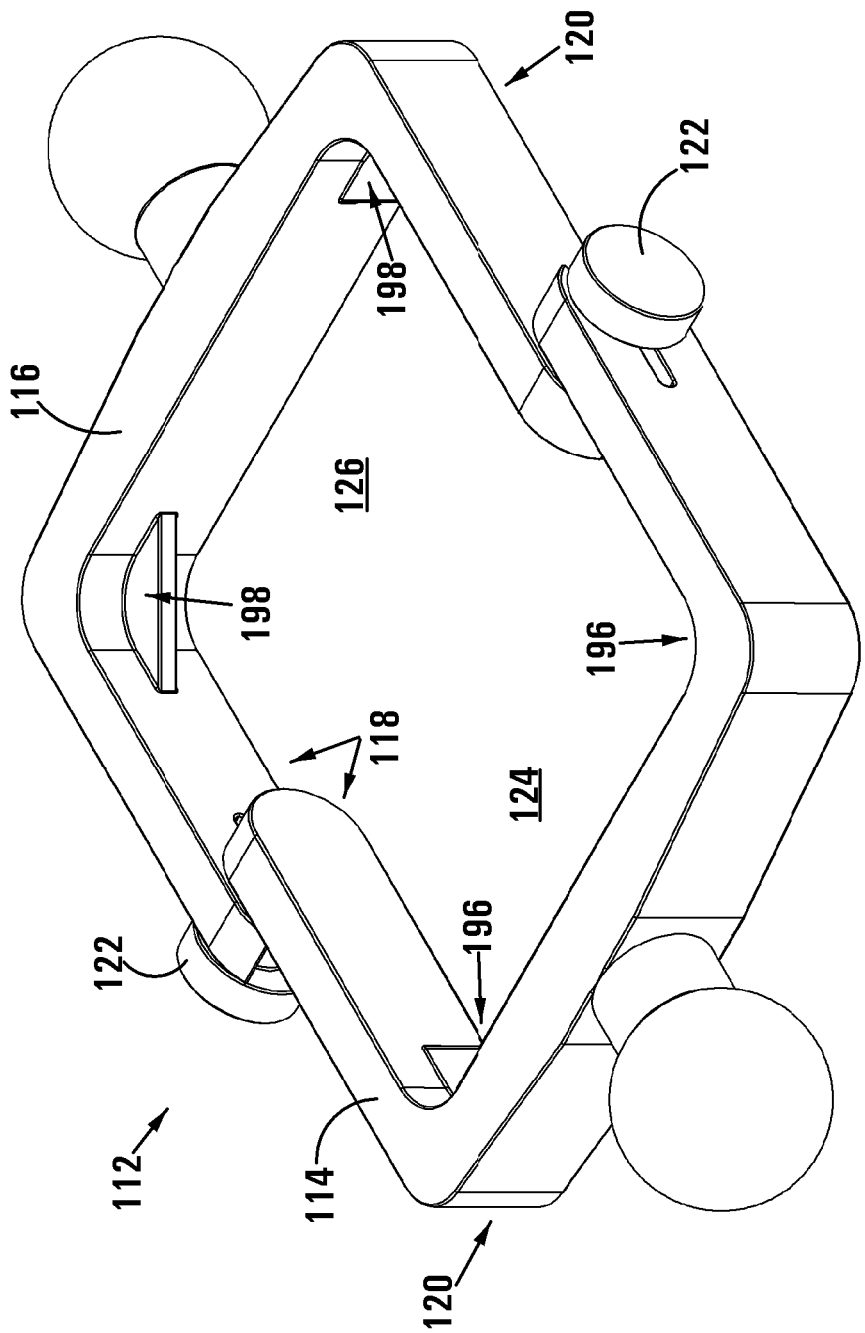
FIG. 12 shows a perspective view of an example articulator to which the stabilizer shown in FIG. 9 can be fitted.

Referring back to FIG. 9 and also to FIG. 10, the vertically adjustable rotational stabilizer 110 comprises a first, upper body 130 secured or securable to one of the support arms 114 of the articulator in FIG. 12. The first body 130 is arranged to be positioned substantially within the opening 124 defined by the support arm 114, the first body 130 defining a seat 132 with an elongate, rectangular aperture 134. The structure of the seat 132 of the first body 130 is substantially similar to the seat 32 described above with reference to the first body 30, and thus similar components are numbered similarly save for the numerical prefix "1". In particular, the seat 132 accommodates a first swivel body, of the type already described above, which can swivel within the seat 132 of the first body 130. In addition, the stabilizer 110 also makes use of an elongate rotational adjusting member, which has already been described above and will thus not be repeated.

Figure 11:
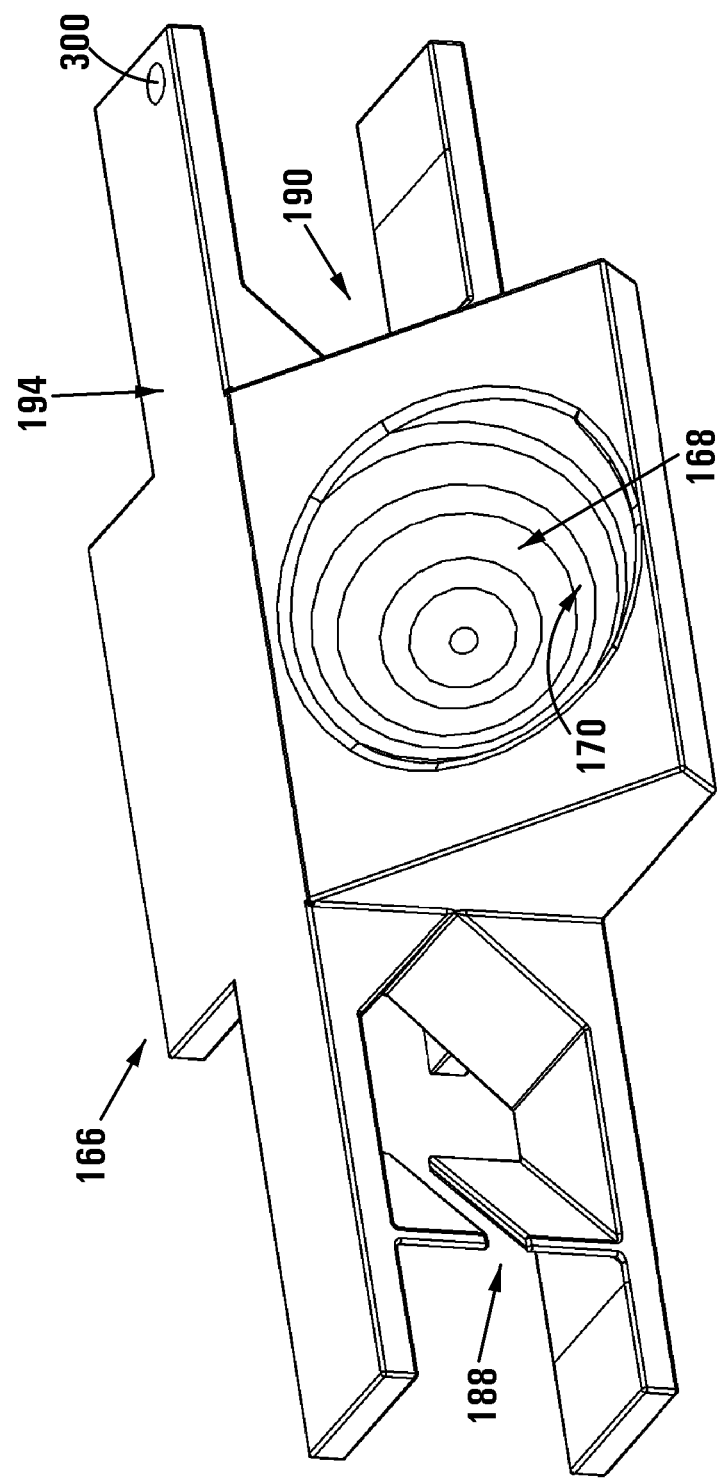
FIG. 11 shows a perspective view of a second, lower body of the stabilizer shown in FIG. 9.

Turning now to FIG. 11, the stabilizer 110 further comprises a second, lower body 166 secured or securable to the other support arm 116 and positioned substantially within the opening 126 defined by the support arm 116. Again, the second body 166 defines a receiving surface 168 against which the distal end 160 of the elongate rotational adjusting member 156 can abut. The entire stabilizer 110 thus allows the relative distance between the distal ends 120 of the support arms 114, 116 to be adjusted (and fixed), as described above.

In one version, the first and second bodies 130, 166 take the form of clip bodies that can be secured to or removably clipped onto the support arms 114, 116 of the articulator 112. In this version, the first and second bodies 130, 166 comprise clipping formations 184 and 186, and 188 and 190, respectively, on wing elements 192, 194 extending from the bodies 130, 166 to enable them to be clipped onto complementary clipping formations 196, 198 on the support arms 114, 116 in a substantially friction fit manner.

As described above, it is envisaged that the clip bodies can simply rest on or be supported by or be glued or cemented to the support arms 114, 116.

Although not shown, in an alternate version, the first and second bodies 130, 166 may be integrally formed with the support arms 114, 116 of the articulator 112.

Figure 13:
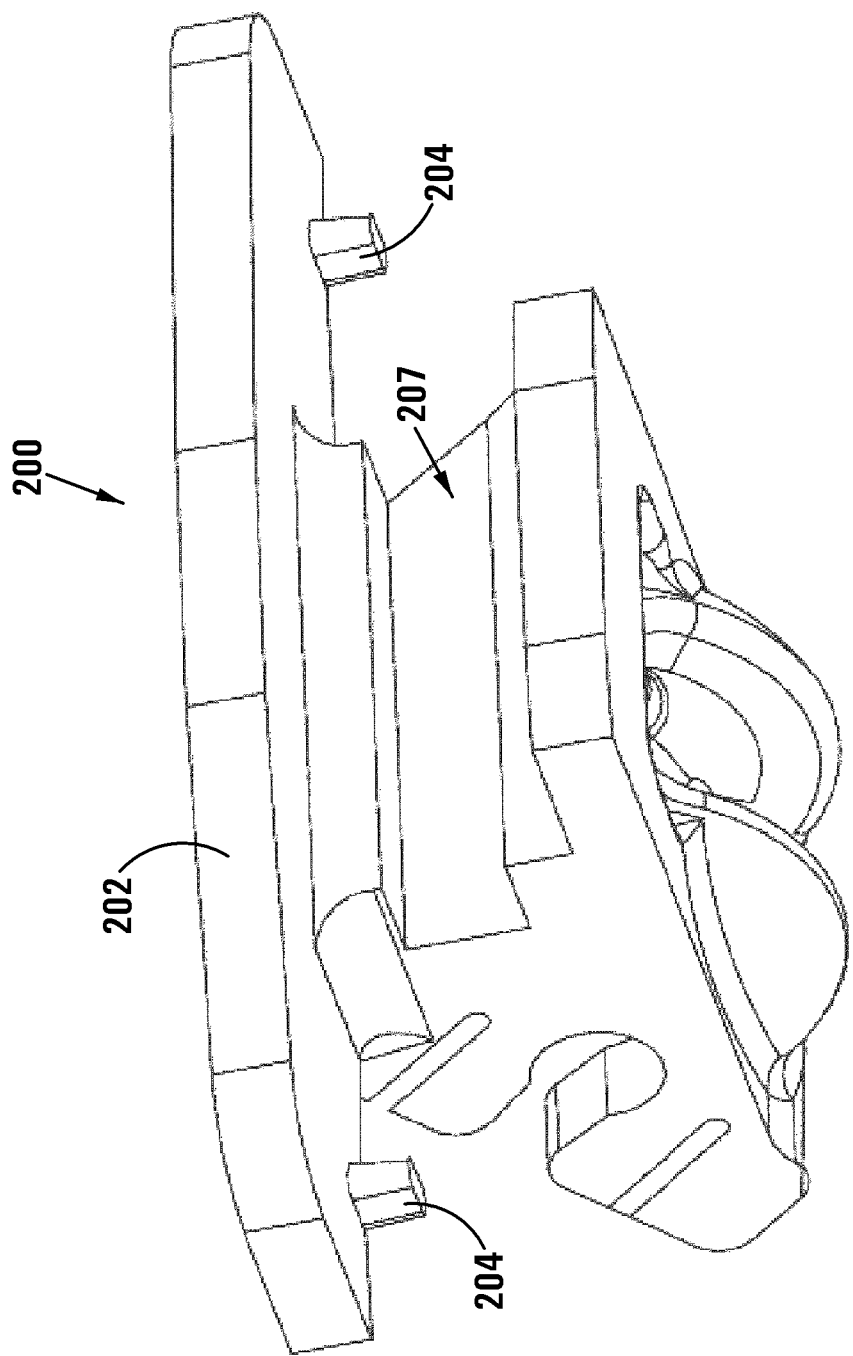
FIG. 13 shows a perspective view of an alternate first, upper body for use in the stabilizer shown in FIG. 9.
Figure 14:
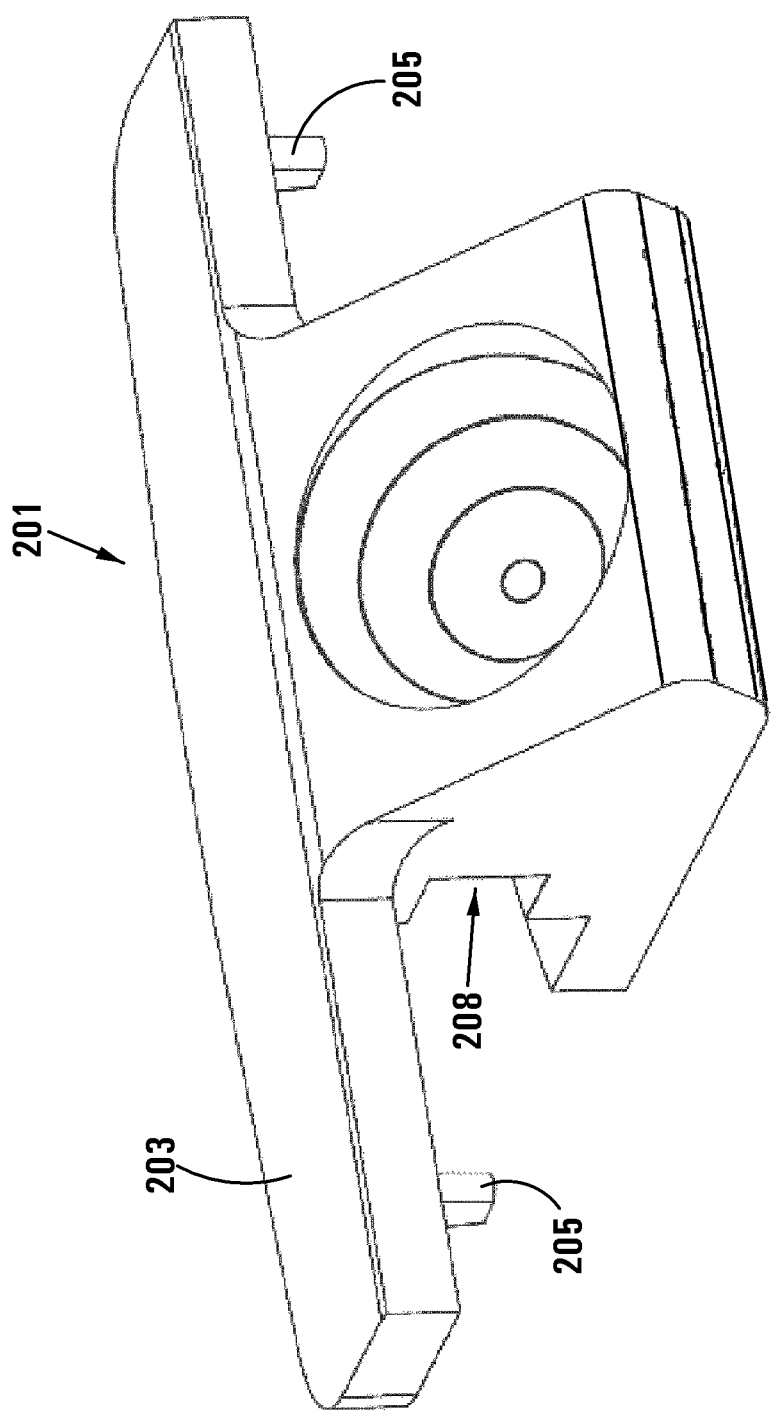
FIG. 14 shows a perspective view of an alternate second, lower body for use in the stabilizer shown in FIG. 9.

In yet a further alternate version, as shown in FIGS. 13 and 14, the first, upper and second, lower bodies 200, 201 only have one wing 202, 203, respectively. In addition, these bodies 200, 201 have guiding pins 204, 205, respectively, to facilitate the positioning of these bodies on the articulator 112. Finally, each body 200, 201 includes a double-stepped recessed arrangement 207, 208, to enable these bodies to be secured to the arms 114, 116 of the articulator 112.

Figure 15:
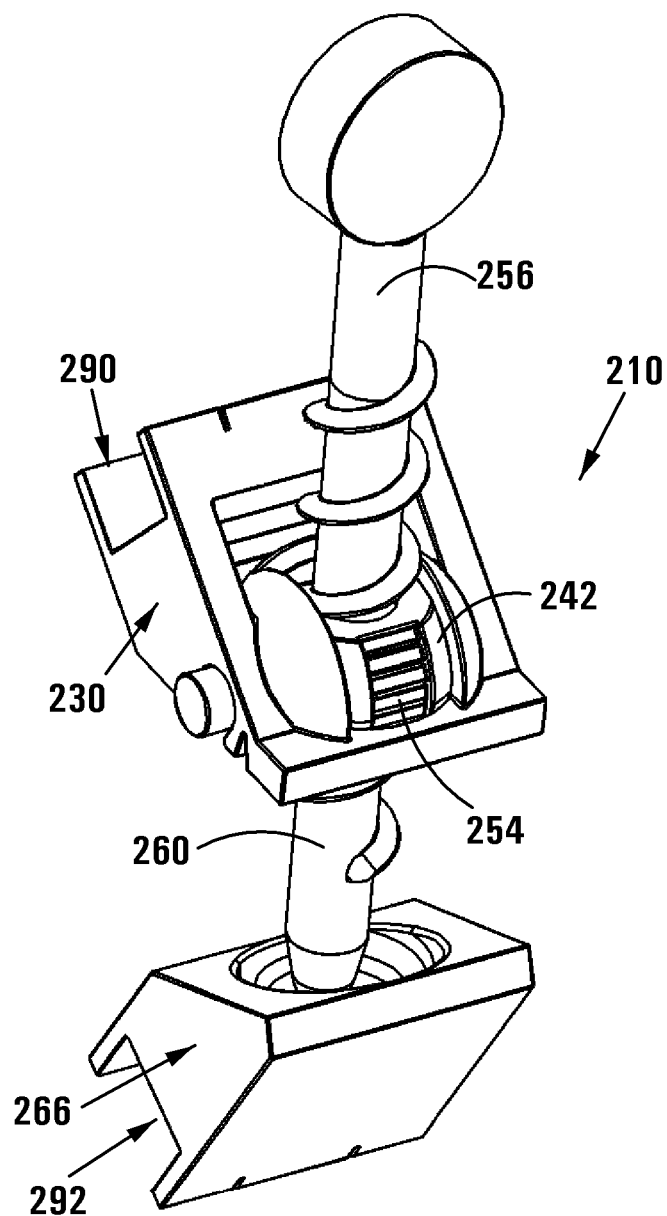
FIG. 15 shows a perspective view of a vertically adjustable rotational stabilizer for a disposable articulator, according to a third embodiment of the present invention.
Figure 16:
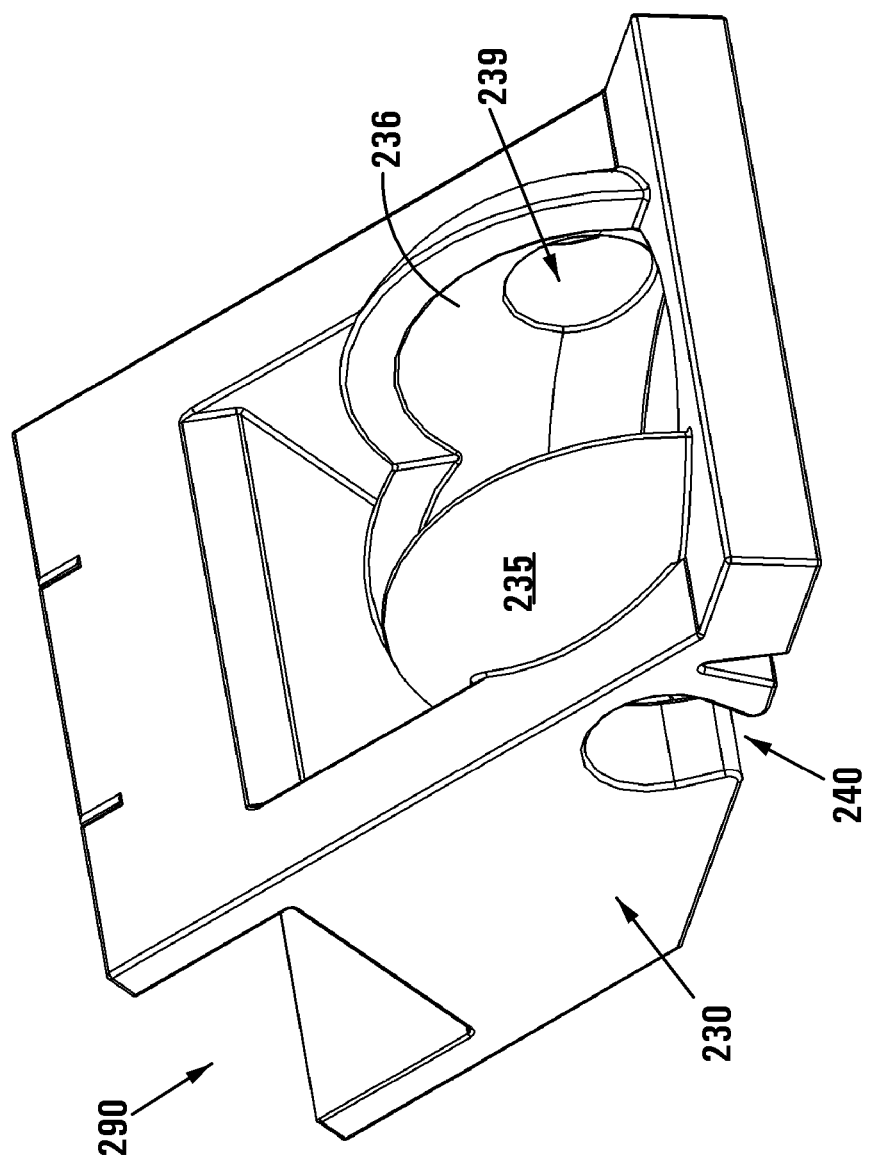
FIG. 16 shows a perspective view of a first, upper body of the stabilizer shown in FIG. 13.
Figure 17:
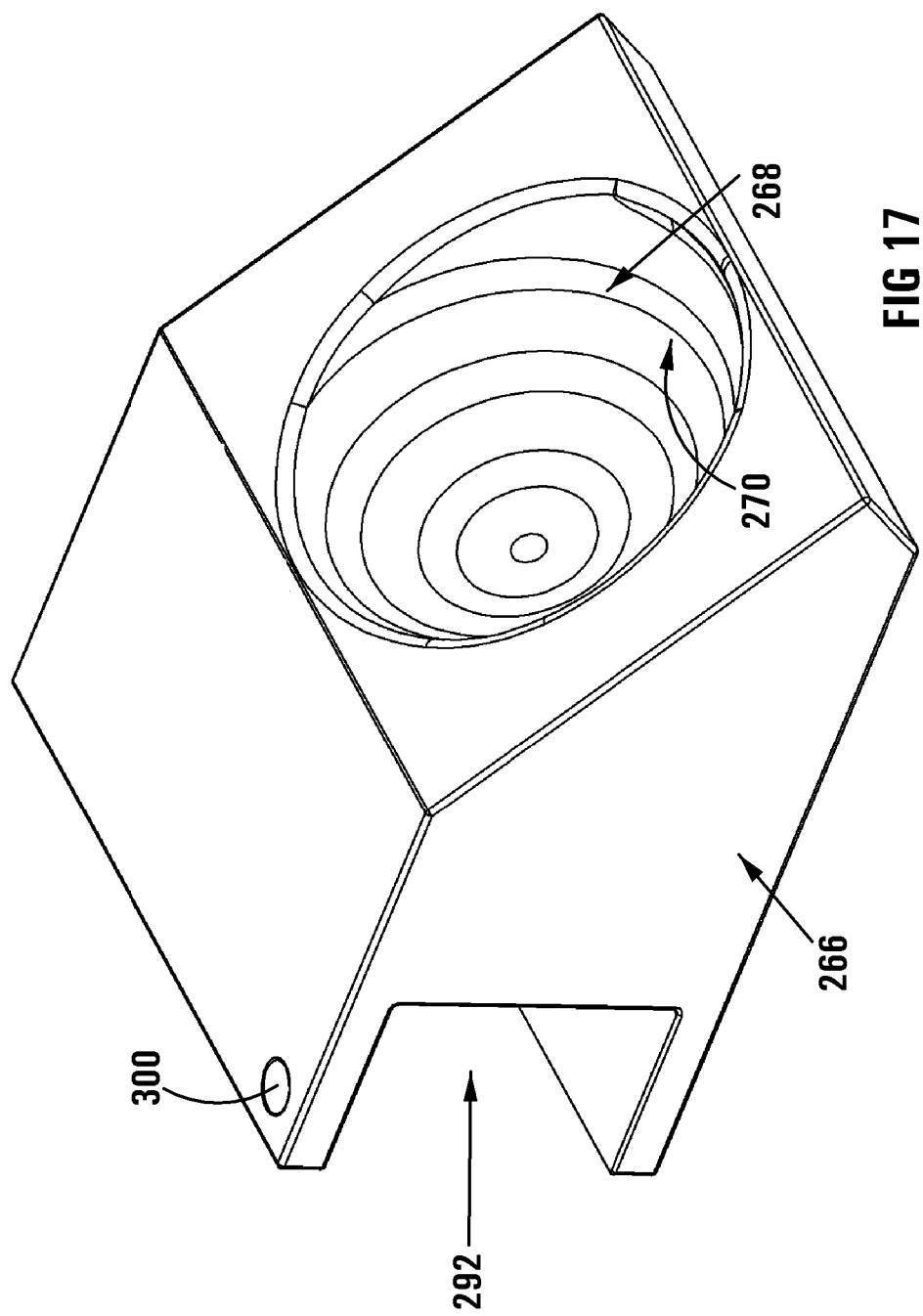
FIG. 17 shows a perspective view of a second, lower body of the stabilizer shown in FIG. 13.

Referring now to FIGS. 15 to 17 there is provided a vertically adjustable rotational stabilizer 210 for the disposable articulator 112 shown in FIG. 12, according to a third embodiment of the present invention. The vertically adjustable rotational stabilizer 210 comprises a first, upper body 230 (which is shown in more detail in FIG. 16) and a second, lower body 266 (which is shown in more detail in FIG. 17), secured or securable to the support arms 114, 116 of the articulator in FIG. 12. The first and second bodies 230, 266 are substantially the same as the first and second bodies 130, 166 described above, save for the omission of the wing elements 184, 186 extending from the bodies 130, 166. The first and second bodies 230, 266 thus simply clip onto the articulator 112 using clipping formations 290, 292 formed on the back of the first and second bodies 230, 266. The first and second bodies 230, 266 can also be secured by a bonding agent or cement. For the rest, the stabilizer 210 operates as described above, which shall not be repeated, except to mention that similar components are numbered similarly save for the numerical prefix "2". Although not shown, in an alternate version, the first and second bodies 230, 266 may be integrally formed with the support arms 114, 116 of the articulator 112.

The stabilizers 10, 110, 210 may carry markings 300 to enable the visually impaired to work with the stabilizers of the present invention.

Although the invention has been described and illustrated with reference to only two currently available articulators 12, 112, the components of the invention, and in particular the bodies 30 and 66, 130 and 166, and 230 and 266, have been designed to be usable on a wide variety of currently available disposable articulators.

Figure 18:
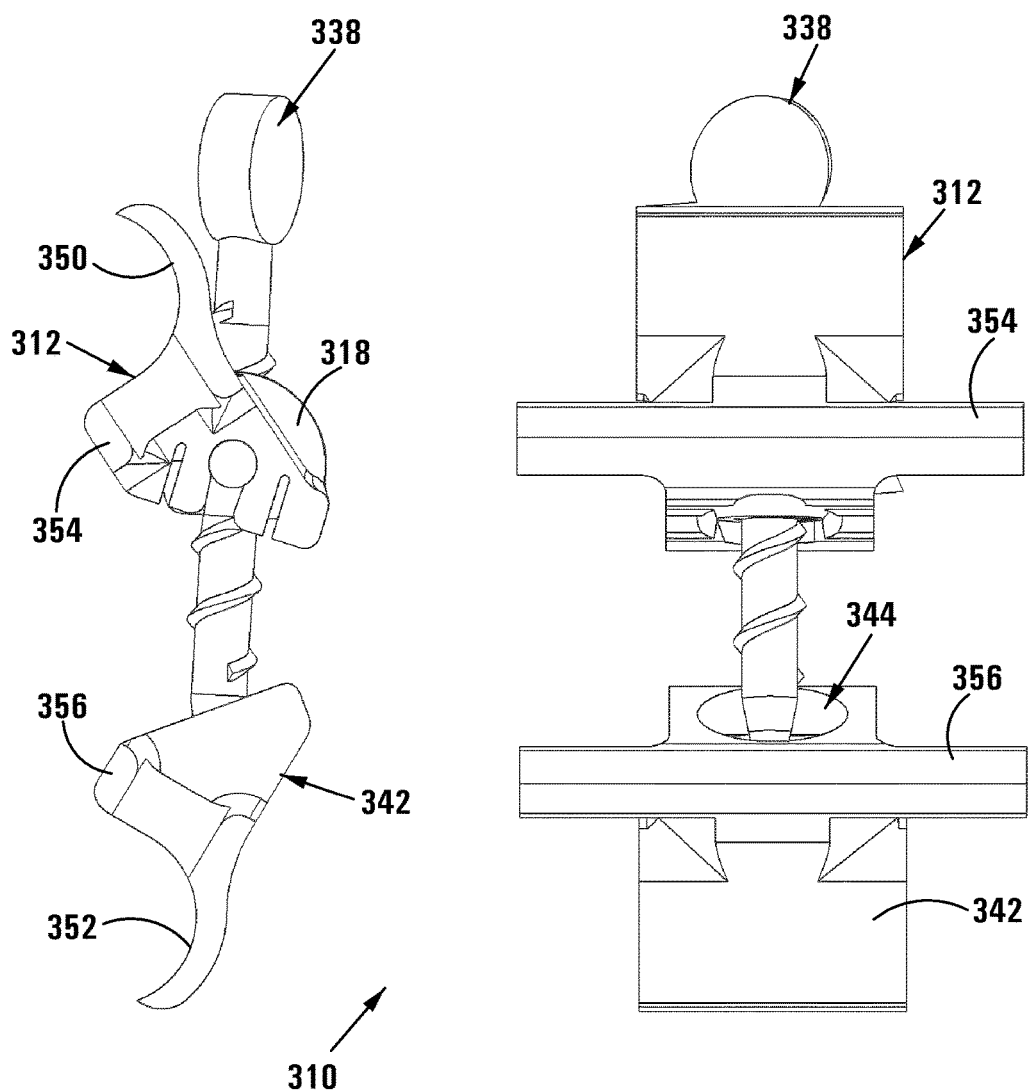
FIGS. 18 to 20 show various views of a vertically adjustable rotational stabilizer for a disposable articulator, according to yet a further embodiment of the present invention.
Figure 19:
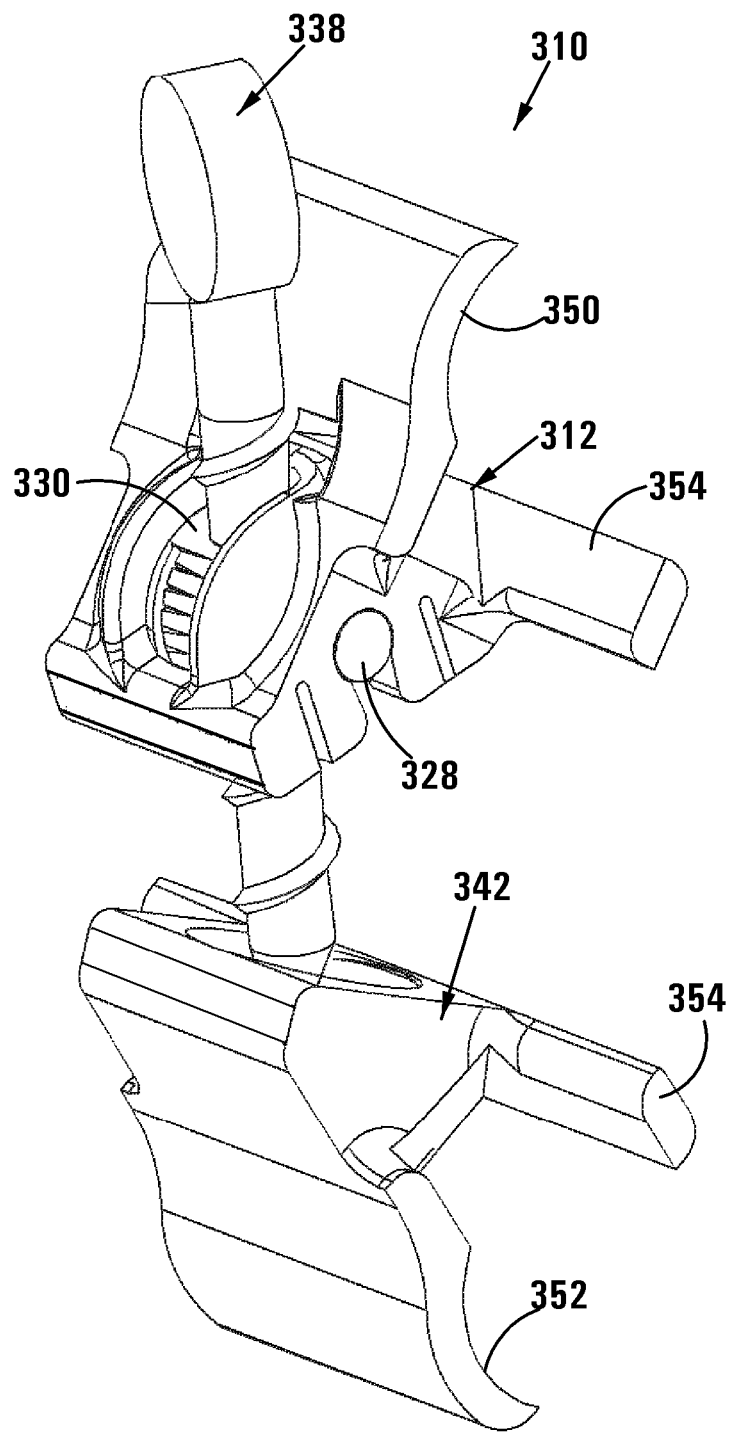
Figure 20:
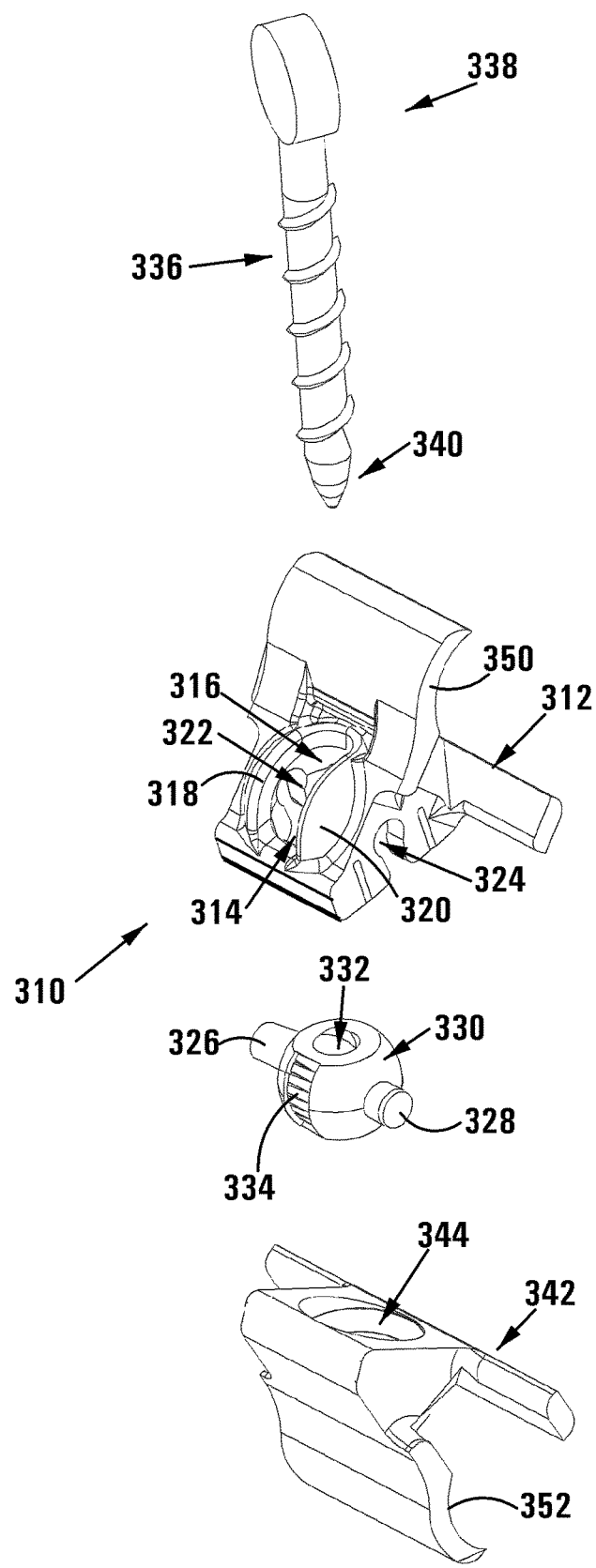

A further embodiment of a vertically adjustable rotational stabilizer 310 will now be described with reference to FIGS. 18 to 20. The vertically adjustable rotational stabilizer 310 comprises a first, upper body 312 secured or securable to a support arm of an articulator. The first body 312 defines a seat 314 with an elongate, rectangular aperture 316.

In an embodiment, the seat 314 of the first body 312 includes a pair of curved side walls 318, 320 that define the aperture 316. The curved side walls 318, 320 define a pair of slots 322, 324 to receive the lugs 326, 328 of a first swivel body 330. The first swivel body 330 is substantially as described above with reference to FIG. 3, and will thus not be described in more detail.

The curved side walls 318, 320 thus accommodate the first swivel body 330 to enable the first swivel body 330 to swivel within the seat 314 of the first body 312 around an axis defined by the lugs 326, 328. The first swivel body 330 has a bore 332 that can align with the aperture 316 in the seat 314 of the first body 312.

Although not marked, the first body 312 includes a pawl proximate the aperture 316 of the seat 314. The first swivel body 330 comprises a plurality of teeth 334 on an exterior surface so as to define a ratchet to facilitate the correct orientation of the first swivel body 330 relative to the first body 312.

The stabilizer 310 further comprises an elongate rotational adjusting member 336 having a proximal end 338 and a distal end 340. The member 336 is arranged to snugly extend through, and be adjustable relative to, the bore 332 of the first swivel body 330. The elongate rotational adjusting member 336 is also arranged to extend through the elongate, rectangular aperture 316 in the seat 314 of the first body 312 when the elongate rotational adjusting member 336 and the first swivel body 330 are seated within the seat 314 of the first body 312, as shown in FIGS. 18 and 19. The remaining components of the elongate rotational adjusting member 336 are as described above.

The stabilizer 310 further comprises a second, lower body 342 secured or securable to the other support arm of an articulator 12. The second body 342 defines a receiving surface 344 against which the distal end 340 of the elongate rotational adjusting member 336 can abut, as shown in FIG. 19 and as described above.

The first and second bodies 312, 342 include curved formations 350, 352, respectively, to accommodate complementally shaped arms of the articulator to which the stabilizer 310 may be fitted. In addition, these bodies 312, 342 include elongate wings 354, 356 to further facilitate the fitment of the bodies 312, 342 to the articulator, although in a further embodiment, these wings 354, 356 may be omitted.

The present invention thus provides a versatile and economical vertically adjustable rotational stabilizer for a disposable articulator. In terms of its versatility, the stabilizers of the present invention can perform the following dental work:

1. Prosthetics/Acrylic Dentures (edentulous dentures/no teeth, full upper denture, full lower denture, partial dentures (no posterior teeth, 2 anterior teeth, or 4 to 8 teeth missing in mouth));
2. Chrome Cobalt/Metal Dentures, or with free end saddles, (edentulous dentures/no teeth, full upper denture, full lower denture, partial dentures (no posterior teeth, 2 anterior teeth, or 4 to 8 teeth missing in mouth));
3. Crown and Bridge/Porcelain Crowns (1 to 3 anterior porcelain crowns with posterior present, 4 to 6 posterior porcelain crowns (upper and lower jaws), posterior cantilever bridges (no posterior teeth support), posterior free end bridges (no posterior teeth support, upper and lower jaws)); and
4. Orthodontics/Teeth correcting Procedures (bite plates and gum guards)

The invention claimed is:

1. A vertically adjustable rotational stabilizer for a disposable articulator, the vertically adjustable rotational stabilizer comprising:
   a first body defining a seat with an aperture therein;
   a first swivel body that can swivel within the seat of the first body, the first swivel body having a bore that can align with the aperture in the seat of the first body;
   an elongate adjusting member having a proximal end and a distal end and being arranged to snugly extend through, and be adjustable relative to, the bore of the first swivel body, the elongate adjusting member also being arranged to extend through the aperture in the seat of the first body when the elongate adjusting member and the first swivel body are seated within the seat of the first body; and
   a second body defining a receiving surface against which the distal end of the elongate adjusting member can abut.

2. The vertically adjustable rotational stabilizer of claim 1, wherein the first swivel body is a truncated sphere that defines two substantially flat faces, with the bore extending through the flat faces of the first swivel body.

3. The vertically adjustable rotational stabilizer of claim 2, wherein the first swivel body further comprises a pair of lugs extending from opposite sides of the first swivel body.

4. The vertically adjustable rotational stabilizer of claim 3, wherein the seat of the first body includes a pair of curved side walls with an elongate groove therebetween so as to define the aperture, the curved side walls defining an aperture and/or a slot to receive the lugs of the first swivel body, the curved side walls thus accommodating the first swivel body to enable the first swivel body to swivel within the seat of the first body around an axis defined by the lugs.

5. The vertically adjustable rotational stabilizer of claim 3, wherein the first body includes a pawl proximate the aperture of the seat, and the first swivel body comprises a plurality of teeth on an exterior surface, approximately midway between the lugs and in line with the bore, so as to define a ratchet to facilitate the correct orientation of the first swivel body relative to the first body.

6. The vertically adjustable rotational stabilizer of claim 1, wherein the elongate adjusting member comprises a handle portion proximate its proximal end and a threaded shank extending from the handle portion and terminating in its distal end, with the bore of the first swivel body being complementarily threaded with respect to the threaded shank, so that the adjusting member is adjustable relative to the first swivel body.

7. The vertically adjustable rotational stabilizer of claim 6, wherein the second body comprises a socket having a curved receiving surface.

8. The vertically adjustable rotational stabilizer of claim 7, wherein the curved receiving surface comprises ridges and/or slots against which the distal end of the elongate adjusting member can rest and/or grip.

9. The vertically adjustable rotational stabilizer of claim 6, wherein the second body defines a seat with an aperture therein, with a second swivel body being able to swivel within the seat of the second body, the second swivel body comprising a socket having a curved receiving surface against which the distal end of the elongate adjusting member can rest and/or grip.

10. The vertically adjustable rotational stabilizer of claim 1, wherein the first and second bodies comprise clips.

11. A disposable articulator comprising:
a hinged pair of support arms, each support arm having a proximal end and a distal end, with the proximal ends of the support arms being hingedly fitted together, with a first support arm defining a first opening between its distal and proximal ends and the second support arm defining a second opening between its distal and proximal ends; and
a vertically adjustable rotational stabilizer comprising:
  a first body secured or securable to the first support arm and positioned substantially within the first opening defined by the first support arm, the first body defining a seat with an aperture therein;
  a first swivel body that can swivel within the seat of the first body, the first swivel body having a bore that can align with the aperture in the seat of the first body;
  an elongate adjusting member having a proximal end and a distal end and being arranged to snugly extend through, and be adjustable relative to, the bore of the first swivel body, the elongate adjusting member also being arranged to extend through the aperture in the seat of the first body when the elongate adjusting member and the first swivel body are seated within the seat of the first body; and
  a second body secured or securable to the other support arm and positioned substantially within the second opening defined by the second support arm, the second body defining a receiving surface against which the distal end of the elongate adjusting member can abut,
  thereby allowing the relative distance between the distal ends of the support arms to be adjusted.

12. The disposable articulator of claim 11, wherein the first and second bodies can be secured or removably clipped onto the support arms.

13. The disposable articulator of claim 11, wherein the first and second bodies are integrally formed with the support arms.

14. The disposable articulator of claim 11, wherein the first and second bodies comprise deformable lugs, which can be snap fitted into corresponding recesses defined in the support arms.

* * * * *